(12) United States Patent
Kojima et al.

(10) Patent No.: US 6,319,378 B1
(45) Date of Patent: Nov. 20, 2001

(54) GAS SENSOR HAVING IMPROVED STRUCTURE

(75) Inventors: Takashi Kojima, Kasugai; Isao Watanabe; Hirokazu Yamada, both of Nagoya, all of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/372,647

(22) Filed: Aug. 12, 1999

(30) Foreign Application Priority Data

Aug. 12, 1998 (JP) .................................................. 10-228356
Dec. 16, 1998 (JP) .................................................. 10-357709

(51) Int. Cl.[7] .................................................. G01N 27/407
(52) U.S. Cl. ............................ 204/427; 204/421; 204/428
(58) Field of Search ...................................... 204/421–429

(56) References Cited

U.S. PATENT DOCUMENTS

| 4,556,475 | * | 12/1985 | Bayha et al. | 204/428 |
| 4,609,454 | * | 9/1986 | Ziegler | 204/428 |
| 4,883,643 | * | 11/1989 | Nishio et al. | 204/428 |
| 5,271,821 | * | 12/1993 | Ogasawara et al. | 204/428 |
| 5,695,625 | * | 12/1997 | Yamada et al. | 204/427 |
| 5,759,365 | * | 6/1998 | Yamada et al. | 204/427 |
| 5,804,050 | * | 9/1998 | Hayakawa et al. | 204/428 |

FOREIGN PATENT DOCUMENTS 2-147817   6/1990 (JP) .
8-160002   6/1996 (JP) .

* cited by examiner

Primary Examiner—T. Tung
(74) Attorney, Agent, or Firm—Pillsbury Winthrop LLP (57) ABSTRACT

An improved structure of a gas sensor is provided which includes a hollow housing and a sensing element. The sensing element has a flange and is disposed within the housing in engagement of the flange with an inner wall of the housing. An insulating powder is packed in a chamber defined by the inner wall of the housing, the flange and an outer wall of the sensing element to provide an air-tight seal between an air chamber to which one end of the sensing element is exposed and a gas chamber to which the other end of the sensing element is exposed. The air-tight seal has the structure designed to minimize an air leakage and breakage of the sensing element when installed in the housing.

6 Claims, 8 Drawing Sheets

GAS SENSOR HAVING IMPROVED STRUCTURE

BACKGROUND OF THE INVENTION

1. Technical Field of the Invention

The present invention relates generally to a gas sensor which may be employed in an air-fuel ratio control system for automotive vehicles for measuring the concentration of gas such $O_2$, $NO_x$, or CO, and more particularly to an improved structure of such a gas sensor which is designed to provide an air-tight seal for avoiding mixing of the air and a gas to be measured.

2. Background Art

Gas sensors constructed of a sensing element for measuring the concentration of a given gas component and a housing having disposed therein the sensing element hermetically are known. In such gas sensors, an upper portion of the gas sensing element is exposed to an air chamber filled with the air that is a reference gas, while a lower portion of the sensing element is exposed to a gas chamber filled with a gas to be measured.

The above gas sensors, however, have the following disadvantages in manufacturing processes.

The sensing element is usually made of a solid electrolyte ceramic to which electrodes and signal output wires are attached and which has a great strength, but is fragile.

The sensing element is in air-tight engagement with the housing to define the air chamber and the gas chamber so that the gas to be measured may be insulated from the air.

In order to increase the degree of air-tightness between the sensing element and the housing, the sensing element may be press-fitted into the housing, but it may cause the sensing element to be broken. Conversely, the press-fit of the sensing element in the housing is loosened in order to avoid such broken, it may cause the air to be mixed with the gas to be measured, thus resulting in a decrease in measurement accuracy.

SUMMARY OF THE INVENTION

It is therefore a principal object of the present invention to avoid the disadvantages of the prior art.

It is another object of the present invention to provide an improved structure of a gas sensor which is designed to provide an air-tight seal between an air chamber and a gas chamber without causing damage to a sensing element during manufacturing.

According to one aspect of the invention, there is provided a gas sensor which may be used in measuring the concentration of a gas. The gas sensor includes: (a) a hollow housing having a first and a second inner wall and a first and a second step projecting inward between the first and second inner walls; (b) a sensing element having a given length, disposed within the housing, the sensing element having a first end portion exposed to an air chamber filled with air and a second end portion exposed to a gas chamber filled with a gas to be measured and having a flange formed between the first and second end portions, the flange being in engagement with the second step of the housing; and (c) an insulating powder packed in a chamber defined by the first step and the first inner wall of the housing and an outer wall of the first end portion of the sensing element to provide an air-tight seal between the air chamber and the gas chamber. If a difference between an inner diameter h of the first inner wall of the housing and an outer diameter S1 of the outer wall of the first end portion of the sensing element (h–S1) is defined as a, and a difference between the outer diameter S1 and an outer diameter S2 of the flange of the sensing element (S2–S1) is defined as b, a relation of $0.2 \leq b/a \leq 0.5$ is met.

In the preferred mode of the invention, a seal ring is disposed between the second step of the housing and the flange of the sensing element.

A cylindrical insulating seal member is further provided which has a tapered outer end portion. The tapered outer end portion is in contact with the insulating powder so as to compress the insulating powder.

An air cover and a gas cover are further provided. The air cover is installed on an end of the housing to define the air chamber. The gas cover is installed on the other end of the housing to define the gas chamber.

According to another aspect of the invention, there is provided a gas sensor which comprises: (a) a hollow housing having a first and a second inner wall; (b) a hollow insulator fitted in the housing, the insulator having a first and a second inner wall and a first and a second step, the first step continuing from the first inner wall, the second step being formed between the first and second inner walls: (c) a sensing element having a given length, disposed within the insulator, the sensing element having a first end portion exposed to an air chamber filled with air and a second end portion exposed to a gas chamber filled with a gas to be measured and having a flange formed between the first and second end portions, the flange being in engagement with the second step of the insulator; and (d) an insulating powder packed in a chamber defined by the second step of the insulator, the first inner wall of the housing, and an outer wall of the first end portion of the sensing element to provide an air-tight seal between the air chamber and the gas chamber. If a difference between an inner diameter h of the first inner wall of the housing and an outer diameter S1 of the outer wall of the first end portion of the sensing element (h–S1) is defined as a, and a difference between the outer diameter S1 and an outer diameter S2 of the flange of the sensing element (S2–S1) is defined as b, a relation of $0.2 \leq b/a \leq 0.5$ is met.

In the preferred mode of the invention, a seal ring is disposed between the second step of the insulator and the flange of the sensing element.

A cylindrical insulating seal member is disposed in the housing so as to compress the insulating powder.

An air cover and a gas cover are provided. The air cover is installed on an end of the housing to define the air chamber. The gas cover is installed on the other end of the housing to define the gas chamber.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
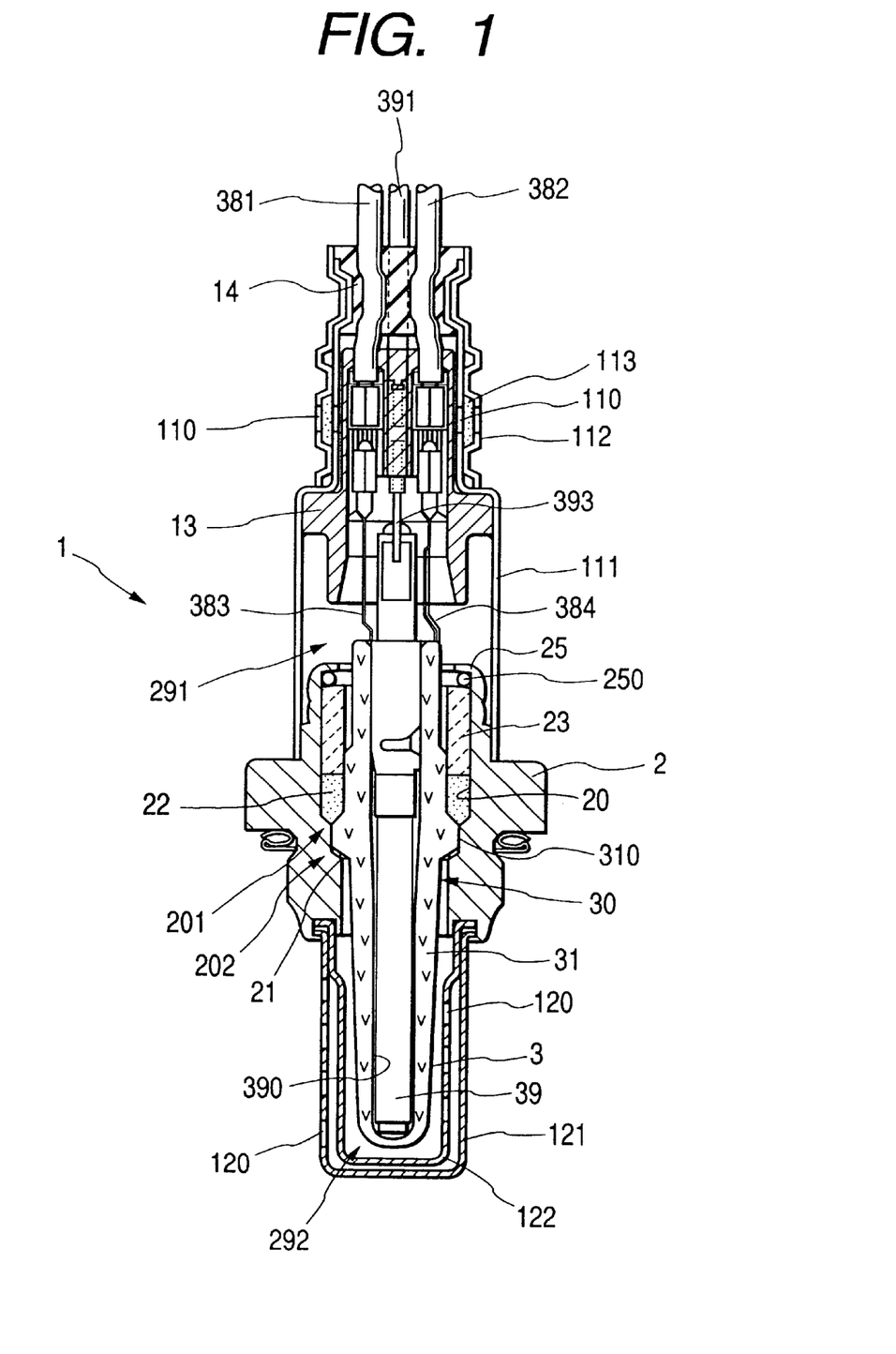
FIG. 1 is a longitudinal cross sectional view which shows a gas sensor according to the first embodiment of the invention.

Referring now to the drawings, wherein like numbers refer to like parts in several views, particularly to FIG. 1, there is shown a gas sensor 1 according to the first embodiment of the invention which may be employed in automotive air-fuel ratio control systems to measure an oxygen content in exhaust gasses of an internal combustion engine.

The gas sensor 1 generally includes a sensing element 3 and a hollow cylindrical housing 2 having disposed therein the sensing element 3 hermetically. The housing 2 also serves as a sensor mount. The sensing element 3 has one end exposed to an air chamber 291 defined by air protective covers 111 and 112 and other end exposed to a gas chamber 292 defined by gas protective covers 121 and 122.

The housing 2 has first and second steps 201 and 202 formed on an inner wall 20 thereof. The sensing element 3 has an outer wall 30 with a flange 310.

The flange 310 is seated on the second step 202 of the housing 20 through a seal ring 21 exposed to the gas chamber 292. A chamber between a portion of the outer wall 30 above the flange 310 and the inner wall 20 of the housing 2 is filled with a seal powder 22 which is compressed by an insulating seal 23 disposed in the housing 2.

Figure 2:
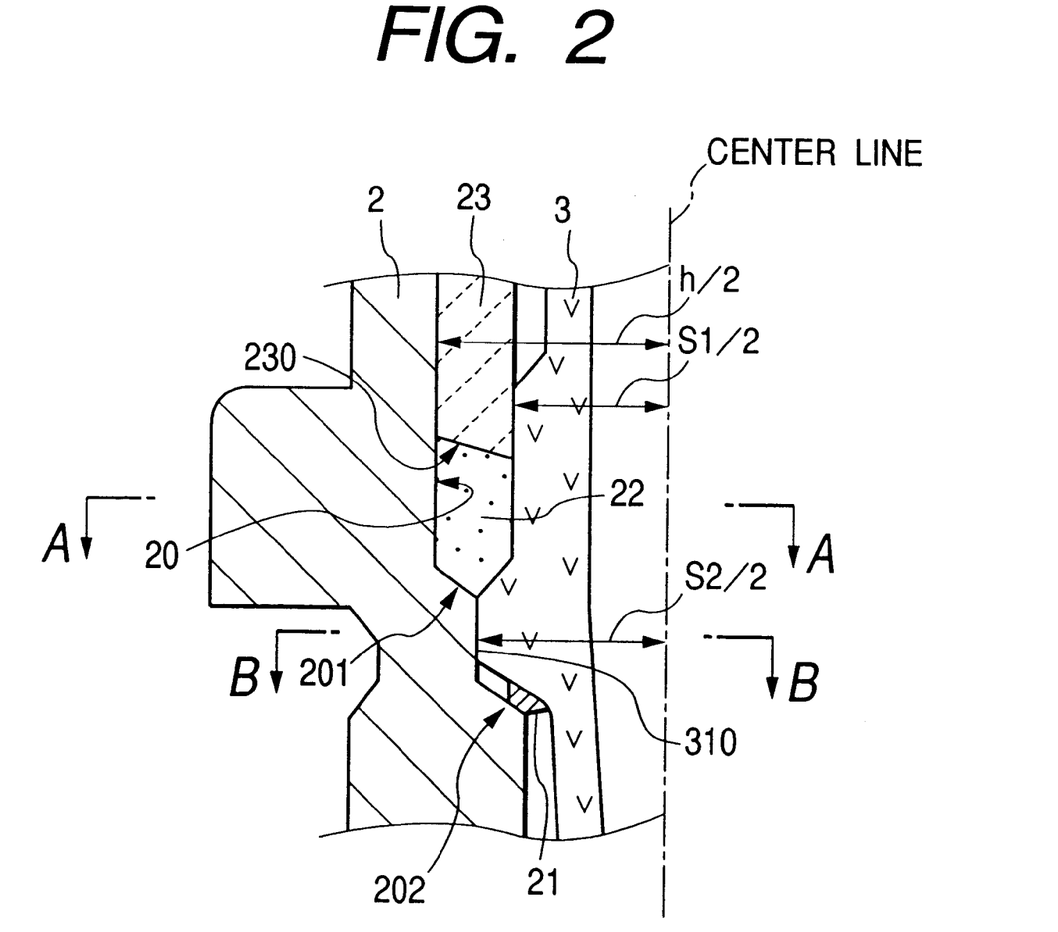
FIG. 2 is a partially sectional view which shows installation of a sensing element in a housing.

If a difference between an inner diameter h of the housing 2, as shown in FIG. 2, communicating with the air chamber 291 and an outer diameter S1 of a portion of the sensing element 3 other than the flange 310 (i.e., h–S1) is defined as a, and a difference between the outer diameter S1 and an outer diameter S2 of the flange 310 of the sensing element 3 (i.e., S2–S1) is defined as b, the relation of $0.2 \leq b/a \leq 0.5$ is, as discussed later in detail, met.

The sensing element 3 is, as described above, fitted in the housing 2. The clearance between the outer wall 30 of the sensing element 3 and the inner wall 20 of the housing 2 is hermetically sealed by the seal ring 21 made of a stainless steel plate, the seal powder 22 made of talc, and the insulating seal 23 formed with a ceramic made of fine alumina. The talc is compressed to have an increased density, resulting in difficulty in penetration of gas therethrough.

The insulating seal 23 is cylindrical and has an outer wall in contact with the inner wall 20 of the housing 2, an inner wall facing with the sensing element 3, and an upper end exposed to the air chamber 291 through a metallic ring 250. The insulating seal 23 also has, as shown in FIG. 2, a tapered bottom 230 in contact with the seal powder 22. The tapered bottom 230 is so shaped that the diameter thereof decreases to the end.

An upper end 25 of the housing 2, as shown in FIG. 1, is crimped inward to produce pressure urging the insulating seal 23 downward through the metallic ring 250. This downward pressure compresses the seal powder 22 to increase the density thereof, thereby enhancing the airtightness.

Figure 3A:
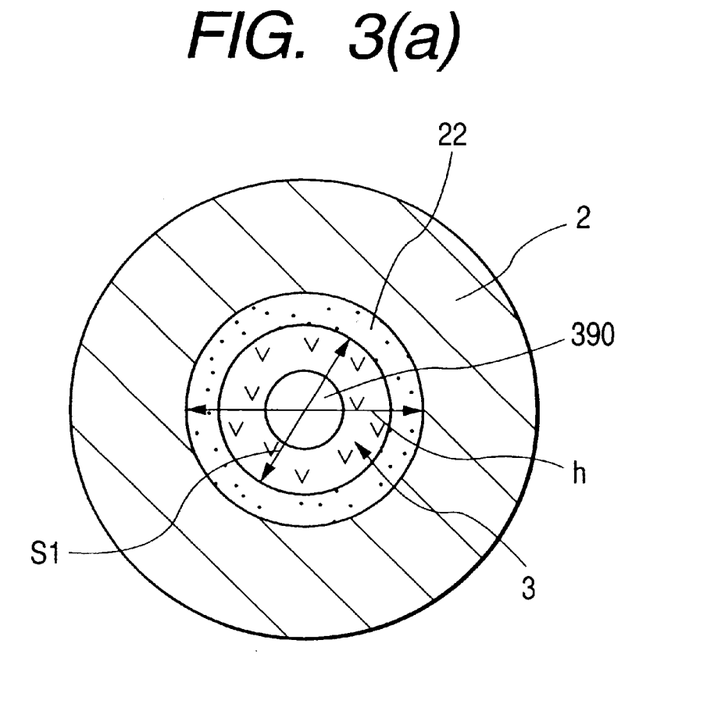
FIG. 3 is a horizontal sectional view taken along the line A—A in FIG. 2 which shows a dimensional relation between a sensing element and a compressed insulating powder.
Figure 3B:
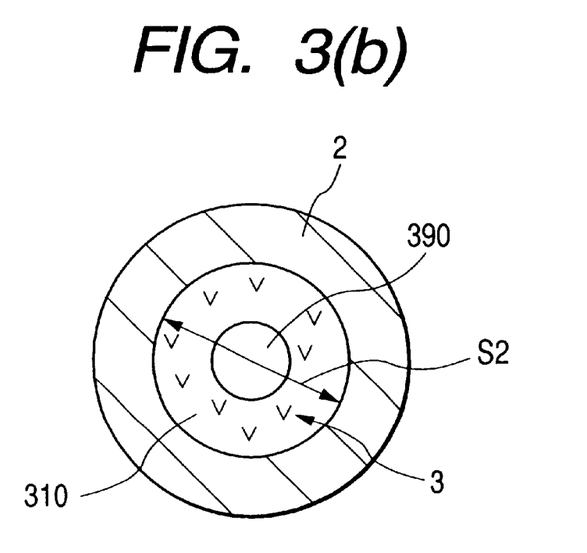
FIG. 3(b) is a horizontal sectional view taken along the line B—B in FIG. 2 which shows a dimensional relation between a flange of a sensing element and a housing.

The inner diameter h, as shown in FIGS. 2, 3(a), and 3(b), of a portion of the housing 2 in contact with the insulating seal 23 is 13.2 mm. The outer diameter S1 of a portion of the sensing element 3 other than the flange 310 is 8.8 mm. The outer diameter S2 of the flange 310 10.4 mm. Thus, b/a (i.e., (S2–S1)/(h–S1)) will be 0.36.

The protective covers 121 and 122 are installed on the bottom of the housing 2 to protect the sensing element 3 and have formed therein gas inlets 120 through which the gas to be measured enters the gas chamber 292.

The air cover 111, as described above, is installed on a flange of the housing 2. The air cover 112 covers the upper end of the air cover 111. The air covers 111 and 112 have air vents 110 formed in alignment which communicate with each other through a water-repellent filter 113 for introducing the reference gas, i.e., the air into the air chamber 291.

Leads 391, 381, and 382 are retained within the air covers 111 and 112 through a rubber bush 14. The leads 381 and 382 connect with the sensing element 3 through connectors and signal pickup lines 383 and 384, respectively. The connectors are disposed within an insulating glass block 13 mounted in the air cover 111. The leads 391 (only one is shown) connect with a heater 39 through terminals 393. The heater 39 is retained within the sensing element 3 and heats the sensing element 3 up to a temperature at which the concentration of gas is allowed to be measured correctly.

The sensing element 3 consists of a cup-shaped solid electrolyte body 31 allowing oxygen ions to pass therethrough and outer and inner electrodes (not shown). The solid electrolyte body 31 is made of a partially stable zirconia and has formed therein an air chamber 390 communicating with the air chamber 291. The outer electrode is attached to the outer wall 30 of the sensing element 3. The inner electrode is attached to the inner wall exposed to the air chamber 390. The outer and inner electrodes are made of Pt. In operation, the electromotive force is produced between the outer and inner electrodes as a function of the concentration of a gas within the gas chamber 292 and outputted electrically through the leads 383 and 384.

For the structure and operation of the gas sensor 1 in more detail, reference is made to U.S. Appln. Ser. No. 09/196,693, filed on Nov. 20, 1998, now U.S. Pat. No. 6,222,372, assigned to the same assignee as that of this application, disclosure of which is incorporated herein by reference.

Figure 4A:
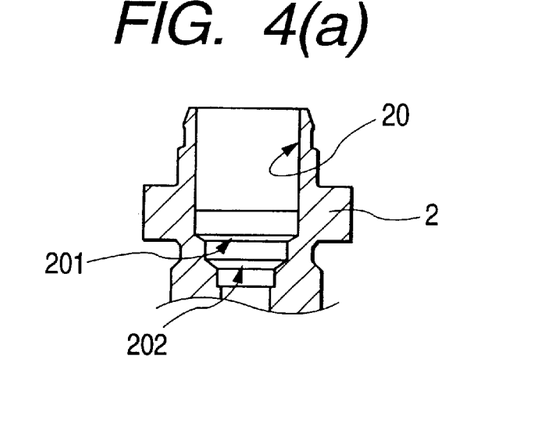
FIGS. 4(a), 4(b), and 4(c) are partially sectional views which show a sequence of assembling processes of a gas sensor.

In assembling of the gas sensor 1, the housing 2 is, as shown in FIG. 4(a), first prepared. The gas protective covers 121 and 122 are installed on the bottom of the housing 2 by inserting ends of the covers 121 and 122, as clearly shown in FIG. 1, into an annular groove formed in the bottom of the housing 2 and crimping a peripheral end wall of the housing 2 inward. Next, the seal ring 21 is placed on the second step 202.

Figure 4B:
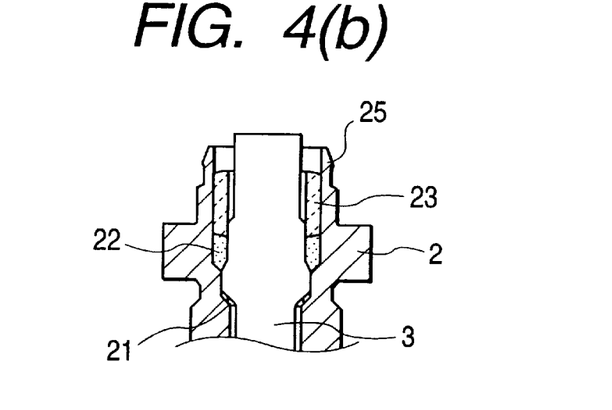

The sensing element 3 is mounted in the housing 2 with the flange 310 seated on the seal ring 21. The seal powder 22 that is the talk is packed in the chamber between the outer wall of the sensing element 3 above the flange 310 and the inner wall of the housing 2. Subsequently, the insulating seal 23 is, as shown in FIG. 4(b), mounted on the seal powder 22 and then pressed downward using a press machine.

Figure 4C:
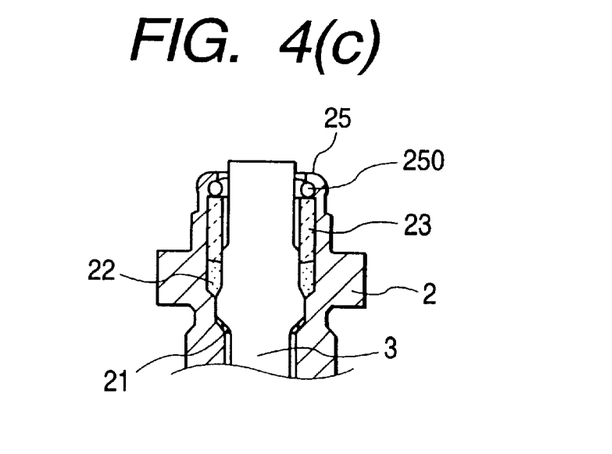

The metallic ring 250 is, as shown in FIG. 4(c), placed on the upper end of the seal powder 22. The upper end 25 of the housing 2 is crimped inward to wrap the metallic ring 250, pressed downward, and at the same time heated electrically to fix the seal powder 22 and the insulating seal 23 firmly, thereby causing the seal powder 22 to be compressed further to enhance the air-tightness between the gas chamber 292 and the air chamber 291.

Subsequently, the heater 39 is mounted in the air chamber 390 of the sensing element 3. The air protective cover 111 is installed at an end on the upper end of the housing 2. The water-repellent filter 113 is mounted around the air protective cover 111 by installing the air protective cover 112 on the upper portion of the air protective cover 111 by crimping.

The insulator 13 and the rubber bush 14 are disposed within the air protective covers 111 and 112. The signal pickup leads 383 and 384 of the sensing element 3 and the terminals 393 of the heater 39 are installed in the insulator 13 and the rubber bush 14. The upper portions of the air protective covers 111 and 112 are crimped or pressed inward to increase the air-tightness of the insulator 13 and the rubber bush 14.

Inventors of this application performed tests for breakage probability and air leakage using six types of samples which have the same structure as the one shown in FIG. 1 and whose b-a ratios (b/a) are 0.1, 0.2, 0.3, 0.4, 0.5, and 0.6, respectively. The results of the tests are shown in a graph of FIG. 5.

The air leakage was measured using an air-leak tester. The breakage probability is expressed in ratio of the number of samples whose sensing elements are broken to the number of tests. The breakage was inspected visually.

Figure 5:
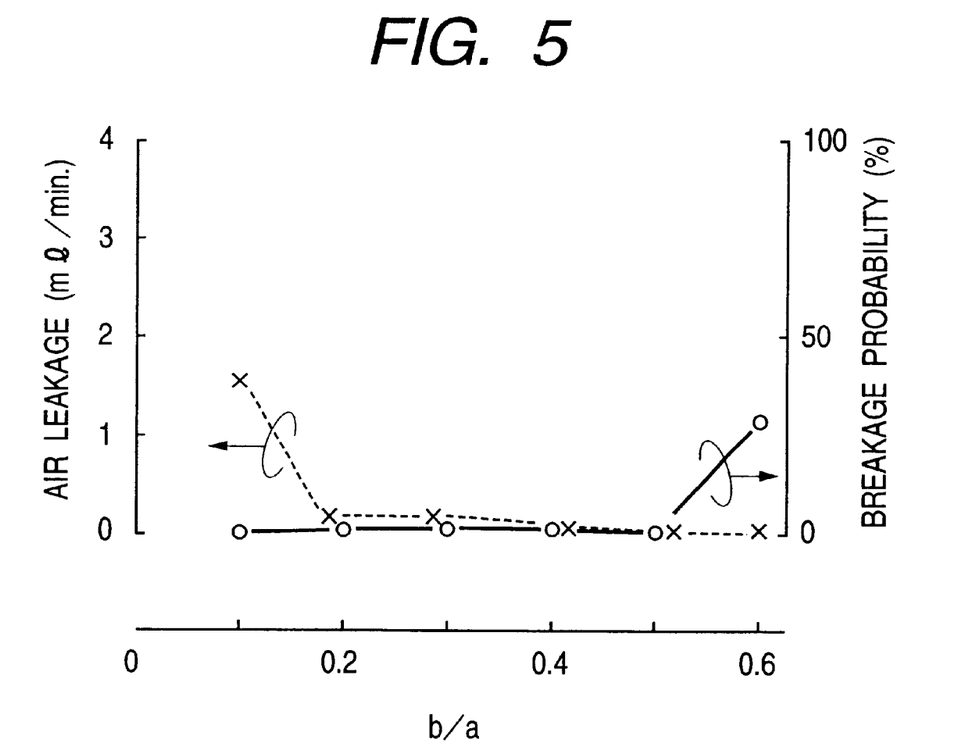
FIG. 5 is a graph which shows test results for breakage probability and air leakage of six types of sample.

The graph shows that when $0.2 \leq b/a \leq 0.5$, the amount of air leakage and the breakage probability are almost zero (0). It was also found that when $b/a<0.2$, the air leakage occurred, and when $b/a>0.5$, the sensing elements 3 in some of the samples were broken when installed in the housings 2, respectively.

In the gas sensor 1 of this embodiment, the ratio of b/a lies within a range of 0.2 to 0.5. It is, thus, appreciated that the air leakage is almost zero, and the sensing element 3 is hardly broken when installed in the housing 2.

The gas sensor 1 is, as described above, designed to produce the electromotive force between the inner electrode exposed to the air chamber 390 and the outer electrode exposed to the gas chamber 292 as a function of the concentration of a gas within the gas chamber 292. If the air leaks out of the air chamber 291 to the gas chamber 291 or the gas leaks out of the gas chamber 292 to the air chamber 390 through the air chamber 291, it may cause the concentration of the gas to be measured in error. The gas sensor 1 of this embodiment provides, as discussed above, the air-tight seal between the gas sensing element 3 and the housing 2, thereby avoiding mixing of the air and the gas to be measured to have high measurement accuracy.

Figure 6:
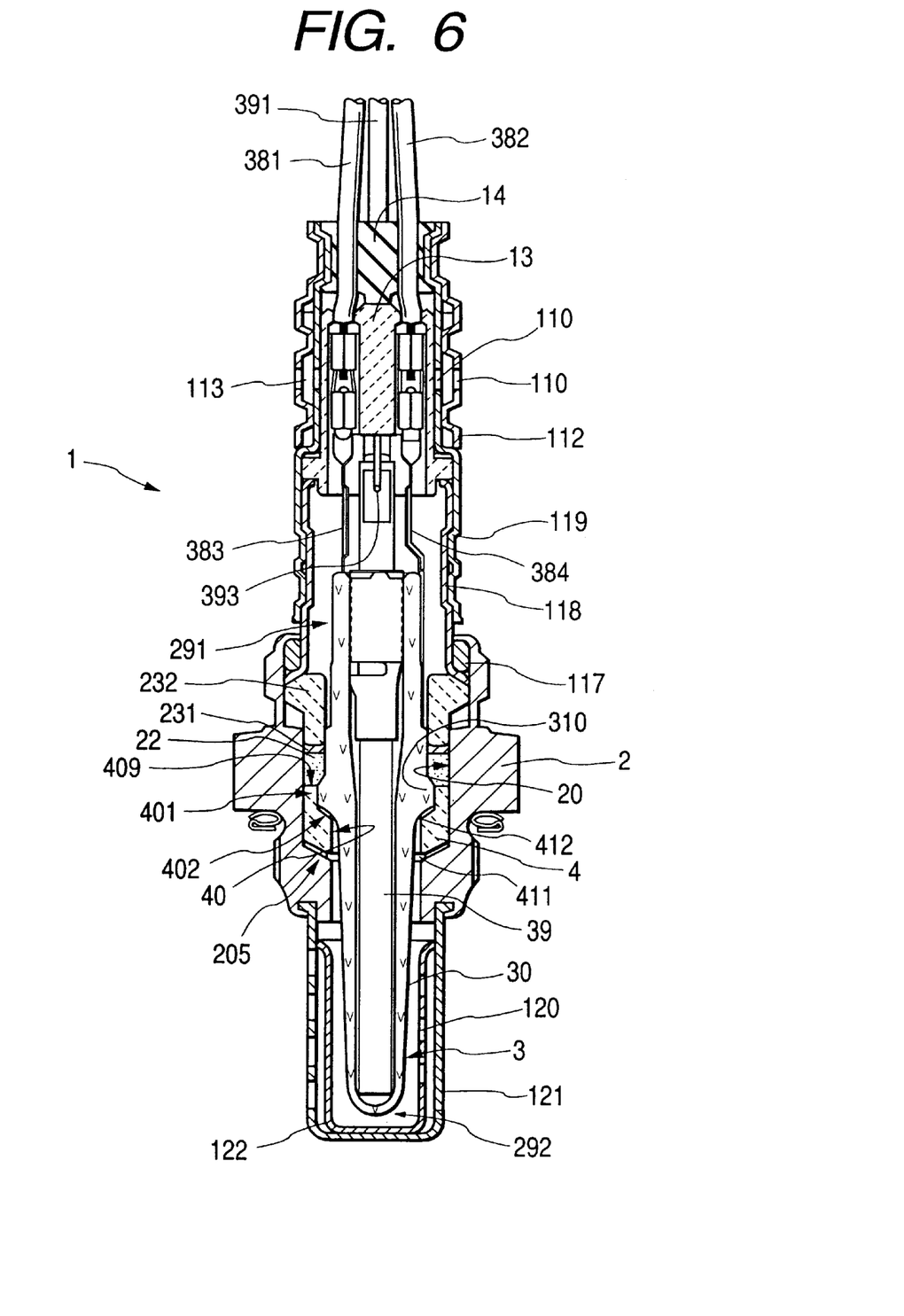
FIG. 6 is a longitudinal cross sectional view which shows a gas sensor according to the second embodiment of the invention.
Figure 7:
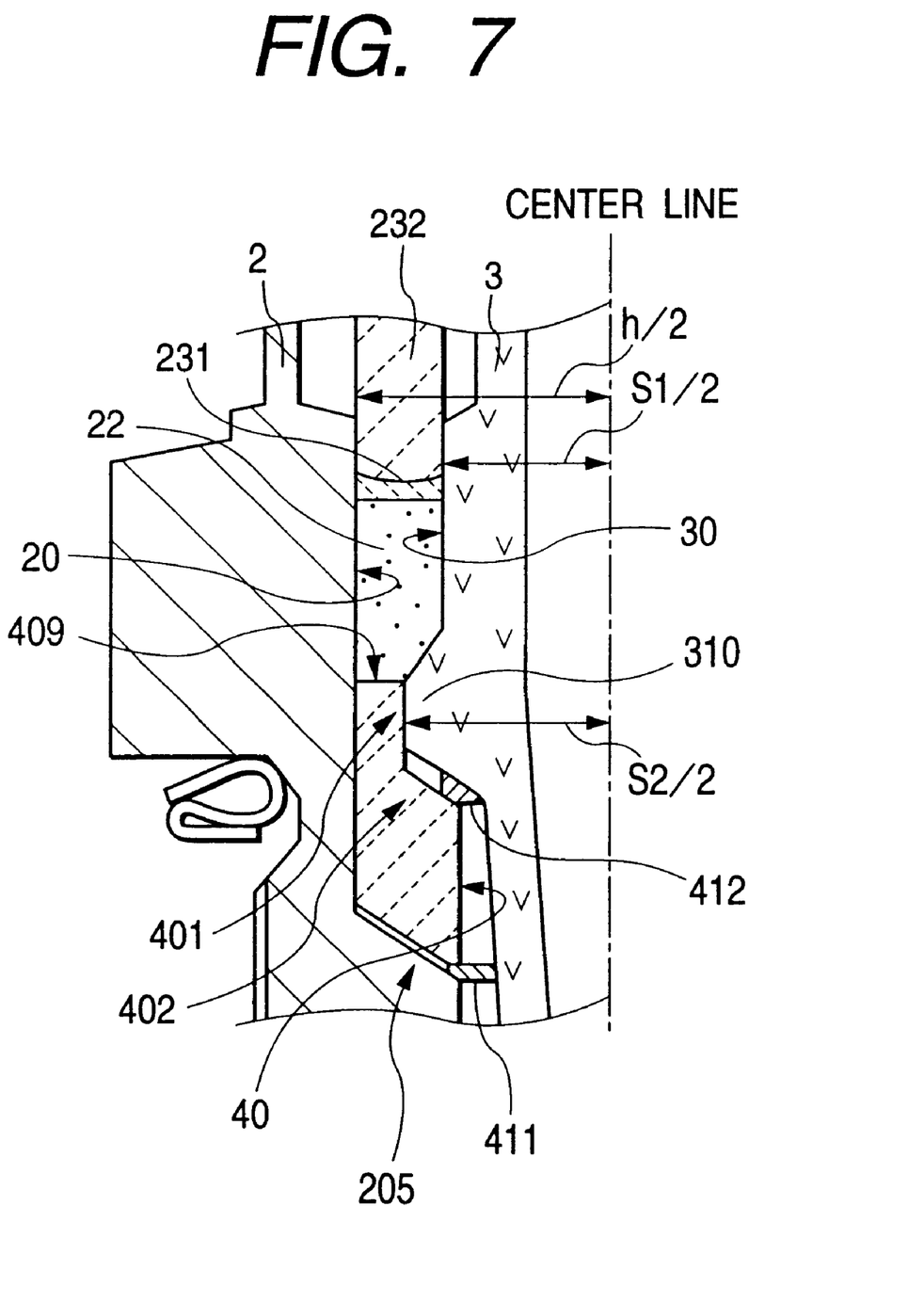
FIG. 7 is a partially sectional view which shows installation of a sensing element in a housing.

FIGS. 6 and 7 show a gas sensor 1 according to the second embodiment of the invention.

The housing 2 has a step 205 formed on the inner wall 20. On the step 205, a hollow cylindrical insulating glass 4 is mounted through a seal ring 411. The insulating glass 4 has a step 402 formed on an inner wall 40 and an inner annular wall 401 formed between an end 409 and the step 402. The sensing element 3 is fitted in the insulating glass 4 in engagement of the flange 310 with the inner wall 401 and the step 402 through a seal ring 412, as clearly shown in FIG. 7. The seal powder 22 is packed in a chamber between the outer wall 30 of the sensing element 3 above the flange 30 and the inner wall 20 of the housing 2 and compressed by insulating members 231 and 232.

An air protective cover 118 is installed at a flanged lower end in the housing 2. The installation of the air protective cover 118 is achieved by crimping an upper end of the housing 2 inward to press the flanged lower end of the air protective cover 118 downward through an annular member 117 such as a metallic ring, thereby compressing the seal powder 22 through the insulating members 232 and 231.

The second air protective cover 119 is installed on an upper portion of the air protective cover 118. The third air protective cover 113 is installed on an upper portion of the second air protective cover 119 through the water-repellent filter 113. The installation of the third protective cover 113 is, as can be seen from the drawing, achieved by crimping outer peripheral portions thereof.

Other arrangements and operation are identical with those of the first embodiment, and explanation thereof in detail will be omitted here.

Figure 8:
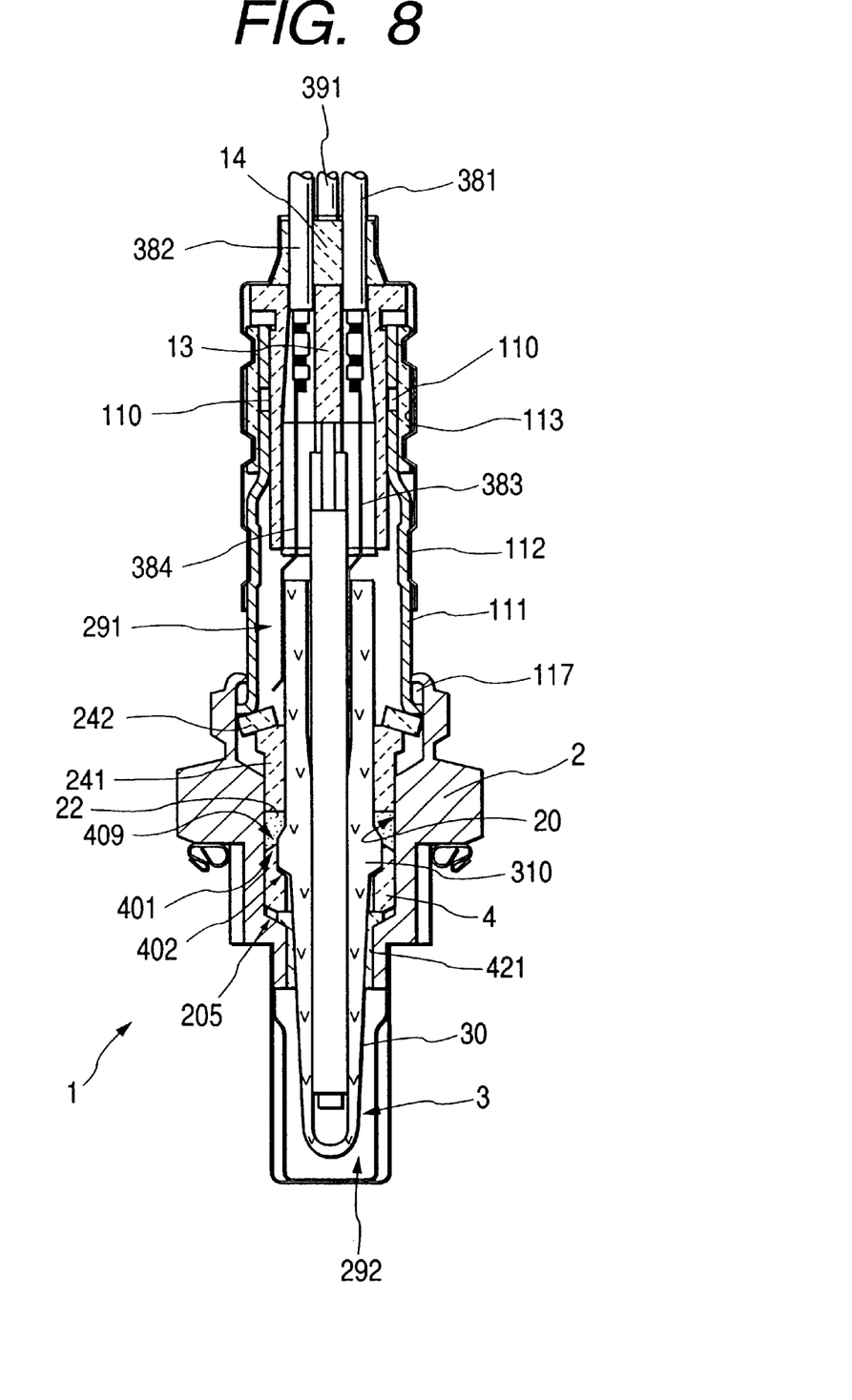
FIG. 8 is a longitudinal cross sectional view which shows a gas sensor according to the third embodiment of the invention.

FIG. 8 shows a gas sensor 1 according to the third embodiment of the invention.

An insulating sleeve 421 is fitted in a lower end of the housing 2 in engagement with the step 205. The insulating glass 4 is mounted in the housing 2 in engagement with the insulating sleeve 421. The insulating glass 4 has the first step 402 on an inner wall thereof and the second step 409 (i.e., an upper end). The sensing element 3 is fitted in the insulating glass 4 in engagement with the first step 402. The seal powder 22 is packed in a chamber between the outer wall 30 of the sensing element 3 above the flange 310 and the inner wall 20 of the housing 2 and compressed by the insulating members 41 and 242.

The air protective cover 111 is installed at a flanged lower end in the housing 2 through the annular member 117 in the same manner as that in the second embodiment. The second air protective cover 112 is installed on an upper portion of the air protective cover 111 through the water-repellent filter 113. Other arrangements and operation are identical with those of the first and second embodiments, and explanation thereof in detail will be omitted here.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

The gas sensor 1 of each embodiment is of the type using the electromotive force, but may be of the type using the limiting current. The gas sensor 1 may include the sensing element 3 formed with laminations. For example, U.S. Pat. No. 5,573,650, issued Nov. 12, 1996 to Fukaya et al., teaches such a structure of the sensing element 3, disclosure of which is incorporated herein by reference.

What is claimed is:

1. A gas sensor comprising:
a hollow housing having a first and a second inner wall and a first and a second step projecting inward between the first and second inner walls;
a sensing element having a given length, disposed within said housing, said sensing element having a first end portion exposed to an air chamber filled with air and a second end portion exposed to a gas chamber filled with a gas to be measured and having a flange formed between the first and second end portions, the flange being in engagement with the second step of said housing;

an insulating powder packed in a chamber defined by the first step and the first inner wall of said housing and an outer wall of the first end portion of said sensing element to provide an air-tight seal between the air chamber and the gas chamber;

a cylindrical insulating seal member having opposing end portions, one end portion being disposed in contact with said insulating powder; and a ring member disposed between a crimped end portion of said hollow housing and an end of said insulating seal member that is opposite to said one end portion, the ring member bearing directly against both the crimped end portion and the opposite end of said insulating seal member so as to transfer elastic pressure produced by the crimped end portion through said insulating seal member and to said insulating powder in order to compress said insulating powder, wherein if a difference between an inner diameter h of the first inner wall of said housing and an outer diameter $S1$ of the outer wall of the first end portion of said sensing element ($h-S1$) is defined as a, and a difference between the outer diameter $S1$ and an outer diameter $S2$ of the flange of said sensing element ($S2-S1$) is defined as b, a relation of $0.2 \leq b/a \leq 0.5$ is met.

2. A gas sensor as set forth in claim 1, further comprising a seal ring disposed between the second step of said housing and the flange of said sensing element.

3. A gas sensor as set forth in claim 1, wherein the one end portion of said insulating seal member is tapered.

4. A gas sensor as set forth in claim 1, further comprising an air cover and a gas cover, said air cover being installed on an end of said housing to define the air chamber, said gas cover being installed on the other end of said housing to define the gas chamber.

5. A gas sensor as set forth in claim 1, wherein a boundary of the flange of said sensing element and said insulating powder and a boundary of the first step of said hollow housing and said insulating powder define a V-shape.

6. A gas sensor as set forth in claim 1, wherein said ring member is substantially circular in cross section.

* * * * *